US012697497B2

(12) United States Patent
Stevenson

(10) Patent No.: US 12,697,497 B2
(45) Date of Patent: Aug. 4, 2026

(54) EMI FILTER FEEDTHROUGH HAVING A SINGLE-SIDED OXIDE-RESISTANT SYSTEM GROUND OPPOSITE A SYSTEM GROUND TO AN OXIDIZED SURFACE

(71) Applicant: Greatbatch Ltd., Clarence, NY (US)

(72) Inventor: Robert A. Stevenson, Canyon County, CA (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 19/196,085

(22) Filed: May 1, 2025

(65) Prior Publication Data

US 2025/0256113 A1     Aug. 14, 2025

Related U.S. Application Data

(63) Continuation-in-part of application No. 18/921,348, filed on Oct. 21, 2024.

(Continued)

(51) Int. Cl.
*A61N 1/375* (2006.01)
*H01G 4/35* (2006.01)
(Continued)

(52) U.S. Cl.
CPC ............. *A61N 1/3754* (2013.01); *H01G 4/35* (2013.01); *H01R 13/40* (2013.01);
(Continued)

(58) Field of Classification Search
CPC ...... A61N 1/3754; A61N 1/3718; H01G 4/35; H01G 4/002; H01G 4/236; H01G 4/228;
(Continued)

(56) References Cited

U.S. PATENT DOCUMENTS 5,978,204 A     11/1999   Stevenson
6,766,779 B2     7/2004   Stevenson et al.
(Continued)

FOREIGN PATENT DOCUMENTS

EP     1 191 556 A2     3/2002
EP     4 548 965 A1     5/2025

OTHER PUBLICATIONS

European App. No. 24 208 767.4—extended European Search Report dated Mar. 12, 2025.

*Primary Examiner* — Travis S Chambers
(74) *Attorney, Agent, or Firm* — Michael P. Scalise

(57)     ABSTRACT

A filtered feedthrough comprises an insulator sealed in a ferrule opening. A terminal pin sealed in an insulator via hole has a first end that extends outwardly beyond an insulator device side. A filter capacitor has a square- or rectangularly-shaped dielectric supporting interleaved active and ground electrode plates. A passageway extending through the dielectric has an internal metallization. An external metallization is contacted to opposed longitudinal sides of the dielectric outer surface. The capacitor ground electrode plates extend to the opposed external metallizations. The outwardly extending terminal pin end is connected to the internal metallization in the dielectric passageway which in turn is connected to the active electrode plates. A conductive material connects the capacitor external metallization at one of the longitudinal sides to an oxide-resistant surface on the ferrule while the other external metallization is connected to an oxidized surface of the ferrule.

19 Claims, 13 Drawing Sheets

Related U.S. Application Data

(60) Provisional application No. 63/595,511, filed on Nov. 2, 2023.

(51) Int. Cl.

| | |
|---|---|
| *H01R 13/40* | (2006.01) |
| *H01R 13/52* | (2006.01) |
| *H01R 13/66* | (2006.01) |
| *H01R 13/719* | (2011.01) |

(52) U.S. Cl.
  CPC ..... *H01R 13/5219* (2013.01); *H01R 13/5224* (2013.01); *H01R 13/6625* (2013.01); *H01R 13/719* (2013.01); *H01R 2201/12* (2013.01)

(58) Field of Classification Search
  CPC ........ H01G 4/232; H01G 2/106; H01R 13/40; H01R 13/5219; H01R 13/5224; H01R 13/6625; H01R 13/719; H01R 2201/12
  See application file for complete search history.

(56) References Cited

U.S. PATENT DOCUMENTS

| | | | |
|---|---|---|---|
| 6,888,715 B2 * | 5/2005 | Stevenson | A61N 1/3754 |
| 9,427,596 B2 | 8/2016 | Brendel et al. | |
| 9,931,614 B2 | 4/2018 | Frysz et al. | |
| 10,272,252 B2 * | 4/2019 | Seitz | A61N 1/3754 |
| 10,350,421 B2 | 7/2019 | Stevenson et al. | |
| 10,449,375 B2 * | 10/2019 | Frustaci | A61N 1/3754 |
| 10,905,888 B2 * | 2/2021 | Stevenson | H01G 4/35 |
| 10,912,945 B2 * | 2/2021 | Stevenson | H01R 4/58 |
| 11,211,741 B2 | 12/2021 | Marzano et al. | |
| 11,241,581 B2 | 2/2022 | Stevenson et al. | |
| 11,344,734 B2 | 5/2022 | Stevenson et al. | |
| 11,633,612 B2 | 4/2023 | Frysz et al. | |
| 2015/0343224 A1 | 12/2015 | Woods et al. | |
| 2017/0291034 A1 | 10/2017 | Marzano et al. | |
| 2018/0236244 A1 | 8/2018 | Stevenson et al. | |
| 2025/0144431 A1 | 5/2025 | Stevenson | |

* cited by examiner

BODY FLUID SIDE

EMI FILTER FEEDTHROUGH HAVING A SINGLE-SIDED OXIDE-RESISTANT SYSTEM GROUND OPPOSITE A SYSTEM GROUND TO AN OXIDIZED SURFACE

CROSS-REFERENCE TO RELATED APPLICATIONS

This application is a continuation-in-part of U.S. patent application Ser. No. 18/921,348, filed on Oct. 21, 2024, which claims priority to U.S. provisional patent application Ser. No. 63/595,511, filed on Nov. 2, 2023.

BACKGROUND OF THE INVENTION

1. Field of the Invention

The present invention generally relates to both implantable and externally worn active medical devices that include a hermetic electromagnetic (EMI) filter feedthrough assembly. More particularly, the present invention relates to an EMI filter feedthrough capacitor, preferably having a rectangular shape, that is grounded to an oxide-resistant surface on only one of its long sides. The opposed long side of the filter feedthrough capacitor is grounded to an oxidized surface. A single-sided oxide-resistant system ground opposite an oxidized system ground for a filter capacitor helps to reduce the complexity and cost associated with building an EMI filter feedthrough assembly, among other benefits. For an asymmetrical hermetically-sealed EMI filter feedthrough assembly relative to the longitudinal axis of its ferrule, a single-sided oxide-resistant system ground opposite a system ground to an oxidized ferrule surface increases the EMI feedthrough capacitor size (width) which makes its design electrically more conservative thereby improving production yields, reliability, and safety factor without unduly sacrificing EMI attenuation afforded by the filter capacitor.

The term "active" is defined as a medical device that includes a power source so that the medical device can deliver an electrical stimulation pulse to body tissue, receive sensed biologic signal from body tissue, or both stimulate and sense.

2. Prior Art

Turning now to the drawings, FIG. 1 is a wire form diagram of a generic human body that is intended to give context to the wide range of active implantable and externally worn medical devices that incorporate a filter feedthrough assembly for attenuation of electromagnetic interference (EMI).

Numerical designation 100A represents a family of hearing devices which can include the group of cochlear implants, piezoelectric sound bridge transducers, and the like.

Numerical designation 100B represents a variety of neurostimulators, brain stimulators, and brain sensors. Neurostimulators are used to stimulate the Vagus nerve, for example, to treat epilepsy, obesity, and depression. Brain stimulators are pacemaker-like devices and include electrodes implanted deep into the brain for sensing the onset of a seizure and also for providing electrical stimulation to brain tissue to prevent a seizure from actually occurring. Sensors include optical sensors, motion sensors, acoustic sensors, pressure sensors, analyte sensors, and electromagnetic sensors, among others.

Numerical designation 100C shows a cardiac pacemaker which is well-known in the art. Cardiac pacemakers include cardiac pacemakers with transvenous leads, leadless pacemakers, and cardiac resynchronization pacemakers, also known as CRT-P devices.

Numerical designation 100D includes the family of left ventricular assist devices (LVADs) and artificial heart devices.

Numerical designation 100E includes a family of drug pumps, which can be used for dispensing insulin, chemotherapy drugs, pain medications, and the like.

Numerical designation 100F includes a variety of bone growth stimulators for rapid healing of fractures.

Numerical designation 100G includes urinary incontinence devices.

Numerical designation 100H includes the family of pain relief spinal cord stimulators and anti-tremor stimulators. Numerical designation 100H also includes an entire family of other types of neurostimulators used to block pain.

Numerical designation 100I includes both implantable cardioverter defibrillator (ICD) devices and congestive heart failure devices (CHF). These are known in the art as cardio resynchronization therapy devices, otherwise known as CRT-D devices.

Numerical designation 100J illustrates an externally worn pack. The pack can be an external insulin pump, an external drug pump, an external neurostimulator or even a ventricular assist device.

Numerical designation 100K illustrates one of various types of EKG/ECG external skin electrodes which can be placed at various external locations on the body.

Numerical designation 100L represents external EEG electrodes that are placed on the head.

In that respect, active medical devices, both implantable and externally worn, have evolved over time to include higher and higher lead counts. For example, in the early days of pacemakers, only the right ventricle was paced. However, design improvements led to dual chamber pacing where the right ventricle and the right atrium are paced. This required two bipolar leads connected to four hermetically-sealed feedthrough terminal pins.

As illustrated is the side cutaway view of a prior art cardiac pacemaker 100C system shown in FIG. 2, with only four terminal pins, it was practical to manufacture round quad-polar filtered hermetic seals or filter feedthrough assemblies. The pacemaker electronics reside inside a hermetically sealed active implantable medical device (AIMD) housing 116 (typically made from titanium), which provides an electrically conductive electromagnetic shield. The header block 101 is typically made from a thermosetting insulating plastic or compound, such as Tecothane®, and houses one or more connector assemblies, generally in accordance with ISO Standards IS-1, IS-2, IS4 or DF4. The header block connector ports (female connectors) are labelled 103, 103'. Implantable leads 107, 107' have proximal plugs 105, 105' (male connectors), which are designed to be inserted into and mate with the female header block connector ports 103, 103'.

Further regarding FIG. 2, the system ground 124 comprises the conductive housing 116, which, as noted above, provides the overall electromagnetic shield, and also functions as an energy dissipating surface. The cardiac pacemaker also has a hermetically sealed feedthrough 120 to which a round quad-polar EMI filter capacitor 132 is mounted. Since the conductive ferrule 112 (typically made from titanium) of the feedthrough 120 is electrically connected to the medical device housing 116, the ferrule 112 is also part of the system ground 124. Accordingly, the system ground 124 illustrated in FIG. 2 includes the ferrule 112 and the device housing 116.

Still referring to FIG. 2, the electrical connection of the EMI filter capacitor 132 to the system ground 124 is better appreciated. When the external ground metallization 142*a* (better shown in FIGS. 3 and 3A for a rectangularly-shaped capacitor) of the EMI filter capacitor 132 is electrically connected to the ferrule 112 of the hermetically sealed feedthrough 120, and the ferrule 112 in turn is hermetically sealed (typically by welding, such as laser welding) to the conductive device housing 116 of the exemplary medical device, for example, a cardiac pacemaker 100C, then the external ground metallization 142*a* is electrically connected to the system ground 124. FIG. 3A shows the external ground metallization 142*a* contacting a gold braze 150 and a continuous gold pad 165 supported on a ferrule 112. The braze 150 seals the ferrule 112 to a metallization 151 on an outer peripheral surface of the feedthrough insulator 160 and contacts a gold pad 165 supported on a device side surface of the ferrule 112. The braze 150 and extended gold pad 165 are formed from one contiguous gold braze at the same time. Exemplary gold pads are shown in FIGS. 21 and 22 of U.S. Pat. No. 6,765,779 to Stevenson et al. The '779 patent is assigned to the assignee of the present invention and incorporated herein by reference.

As schematically depicted in FIG. 3B, an EMI filter capacitor 132 is a three-terminal device in that there is an input side (terminal circle 1), an output side (terminal circle 2) and a ground (terminal three). It is well known that an implanted lead can undesirably act as an antenna and couple to high frequency electromagnetic interference (EMI) energy. This EMI energy may be undesirably coupled along the implanted leads 107, 107' (FIG. 2), which is then directed to sensitive electronics 140 contained inside the device housing 116. It is well known that EMI can disrupt the proper operation of the electronic circuitry 140. Thus, the function of the feedthrough capacitor 132 illustrated in FIGS. 2 and 3 is to couple to incoming EMI energy in the implanted lead and divert it to the electromagnetically shielded device housing 116 comprising the equipotential system ground 124 where the EMI energy will be dissipated as a harmless amount of thermal or RF energy.

In other words, it is the job of feedthrough capacitor 132 to protect the sensitive electronics 140 while at the same time freely allowing pacing or therapeutic pulses to pass and also to allow the device electronics 140 to sense biological signals that are generally in the frequency range from zero to 2000 Hz without interruption. The capacitor 132 is also known as a frequency variable impedance element. The capacitive reactance $X_c$ in ohms: $X_c=1/[2\pi fc]$. This inverse relationship with frequency means that at very low frequencies, the capacitor 132 acts as an open circuit (as if it were not there at all). At very high frequencies, the capacitor 132 substantially acts as a short circuit where it diverts undesirable RF energy such as emissions from cellular telephones, microwave ovens, and the like, to the system ground 124. In that manner, dangerous EMI energy is prevented from entering the device housing 116 where it could reach the sensitive electronic circuitry 140 and seriously disrupt the proper operation of any one of the above-described medical devices 100A to 100L. Such EMI disruption could inadvertently suspend therapy, which, depending on the medical device, could be immediately life threatening.

It is also within the scope of the exemplary cardiac pacemaker 100C system shown in FIG. 2 (or any of the other medical devices depicted in FIG. 1) that the ferrule 112 can be a continuous part of the device housing 116. This means that the ground metallization 142*a*, the ferrule 112, the gold braze/contact pad 165 (FIGS. 3 and 3A) and the medical device housing 116 are all at the same potential; they are all at ground potential and are all part of the overall active medical device equipotential surface (in other words, system ground 124). Since the hermetically sealed enclosure of the medical device blocks EMI from entering inside the device housing 116, it is commonly known as an EMI shield or a Faraday cage.

However, modern cardiac implantable electronic devices (CIEDs) provide therapeutic pacing and biologic signal sensing to chambers in both the right and left sides of the heart. These are known as cardiac resynchronization devices. CRT-P devices are cardiac resynchronization therapy-pacemaker devices. CRT-D devices are cardiac resynchronization therapy-defibrillator devices. These resynchronization devices have hermetic feedthroughs with more than four terminal pins, for example, 8, 11, 13, 16, and more terminal pins. Neurostimulators, such as spinal cord stimulators, generally have greater than 25 terminal pins and possibly as many as 35 terminal pins.

For patient comfort, for example, in the pectoral pocket, it is very important that a filter feedthrough assembly is as thin as possible. However, as the number of hermetically-sealed feedthrough terminal pins that are connectable to associated implantable leads has increased over time, a round or square hermetic seal geometry is no longer desirable or practical. Round, high terminal pin count filter feedthrough assemblies are much too large in diameter for acceptable patient comfort. For that reason, most present-day EMI filter capacitors for hermetic feedthroughs are rectangular with the terminal pins aligned inline or in dual inline configurations to achieve both the required high terminal pin count and the desired device thinness.

Turning now to FIGS. 3, 3A and 3B, these drawings illustrate an exemplary conventional or prior art rectangularly-shaped EMI filter feedthrough assembly 210 having inline terminal pins. The filter feedthrough assembly 210 comprises an electrically conductive ferrule 112 having a ferrule opening extending to spaced-apart ferrule device and body fluid sides. Preferably, the ferrule 112 has a rectangular shape so that in a plan view, looking at either of the ferrule device or body fluid side, the ferrule comprises opposed ferrule first and second longitudinal sidewalls 112A and 112B that extend to and meet with opposed ferrule third and fourth end walls 112C and 112D. The longitudinal sidewalls 112A, 112B are longer than the end walls 112C, 112D and are aligned substantially parallel to and on opposite sides of a ferrule center line (FIG. 3A) that intersects the opposed third and fourth end walls 112C, 112D.

The filter feedthrough assembly 210 further comprises an electrically non-conductive insulator 160, preferably made from alumina, having an insulator outer surface that extends to spaced-apart insulator device and body fluid sides. The insulator 160 is hermetically secured to the ferrule 112 in the ferrule opening by a first gold braze 150 that seals around the perimeter of the insulator. That way, when the ferrule 112 hermetically sealed to the insulator 160 is attached to an opening in a housing of any one of the above-described medical devices 100A to 100L, the ferrule and insulator body fluid sides, and the opposed ferrule and insulator device sides reside outside and inside the medical device, respectively.

Further, at least two, and preferably a plurality of, insulator via holes 126 extend to the insulator device and body fluid sides. Respective outer and inner insulator metallizations 151, 153 are disposed on the perimeter outer surface and in the via holes 126 of the insulator. These metallizations 151, 153 can be applied by sputtering, electroplating, physical vapor deposition or glass frit metallization bonding, and may comprise titanium, molybdenum, niobium, silver, copper, platinum, palladium, platinum silver, palladium silver, and combinations thereof.

A respective one of at least two, and preferably a plurality of, terminal pins (FIG. 3 shows an exemplary number of terminal pins 111*a*, 111*b*, 111*c* and 111*d*) reside in one of the insulator via holes 126 where a second gold braze 162 hermetically seals the terminal pin to the inner metallization 153 contacted to the insulator 160 in the via hole 126. The terminal pins 111*a*, 111*b*, 111*c* and 111*d* extend to first and second ends with at least the terminal pin first ends extending outwardly beyond the insulator device side.

The filter feedthrough assembly 210 further comprises a filter feedthrough capacitor 132 that is mounted adjacent to the insulator device side of the feedthrough 120. The filter capacitor 132 has a rectangularly-shaped or square-shaped, preferably rectangularly-shaped, dielectric 122 supporting interleaved active and ground electrode plates 146 and 148. A plurality of inline passageways 143 extend through the dielectric 122. Each passageway 143 has an internal metallization 144. The metallized inline passageways 143 are electrically connected to the active electrode plates 146 but not to the ground electrode plates 148. An insulative washer 212 extending across the bottom of the EMI filter capacitor 132 rests on top of the device side of the ferrule 112 hermetically sealed to the insulator 160.

The rectangularly-shaped feedthrough capacitor dielectric 122 has opposed relatively long longitudinal sides 122A and 122B that extend to and meet with relatively short ends 122C and 122D. External metallizations 142*a* and 142*b* are contacted to the respective longitudinal sides 122A and 122B of the capacitor dielectric 122. If desired, the opposed short ends 122C, 122D can also be terminated, but that is optional.

The ground electrode plates 148 extend to the external metallizations 142*a*, 142*b* at the terminated longitudinal sides 122A, 122B of the dielectric 122. The outwardly extending ends of a corresponding number of the inline terminal pins 111*a*, 111*b*, 111*c* and 111*d* comprising the feedthrough 120 are received in the dielectric passageways 143 where they are connected to the internal metallization 144 by an inner electrically conductive material 156. The inner conductive material 156 electrically connects the metallized dielectric passageways 143 to the interleaved active electrode plates 146.

An outer conductive material 152 electrically connects the capacitor external metallizations 142*a*, 142*b* at the opposed terminated longitudinal sides 122A, 122B of the rectangularly-shaped dielectric 122 to a gold braze 150 that hermetically connects the insulator outer perimeter metallization 151 to the ferrule 112 comprising the previously described system ground 124. A gold contact pad 165 is shown as a continuous body with the braze 150.

As shown in FIGS. 3 and 3A, to provide a larger oxide-resistant electrical connection, an oxide-resistant material 165, preferably gold, in the form of a contact pad is supported on the device side surface of the ferrule 112 adjacent to the gold braze 150. Preferably, the outer conductive material 152 is contacted to both the gold braze 150 and to the gold contact pad 165 to provide a desirably very low impedance and very low resistance electrical connection. Suitable outer conductive materials 152 include a solder, a thermosetting electrically conductive adhesive, an electrically conductive silicone, a braze, an electrically conductive polyimide, an electrically conductive epoxy, and the like.

However, there have been efforts to improve the insertion loss or filter attenuation of the filter feedthrough assembly 210 illustrated in FIGS. 3, 3A and 3B to meet the needed performance requirements for both MRI compatibility and compatibility with industry standard ISO14117. That is because connecting to the perimeter gold braze 150 hermetically sealing between the outer metallization 151 on the perimeter of the insulator 160 and the ferrule 112 in the ferrule opening can result in the filter capacitor 132 having a truncated lateral extent. The gold contact pad 165 located immediately adjacent to the gold braze 150 helps to widen the lateral extent of the low impedance and low resistance electrical connection between the ground electrode plates 148 and the ground metallizations 142*a*, the ferrule 112 and the medical device housing 116 comprising the system ground 124. However, providing an oxide-resistant contact pad 165 adjacent to both ground metallizations 142*a* and 142*b* represents an added expense in gold that could be avoided with a redesigned filter feedthrough.

Accordingly, there is a need for a redesigned filter feedthrough assembly where the ground electrode plates of the filter capacitor are attached to a system ground in a low impedance and low resistance electrical connection, but that also considers the added expense attributed to providing gold contact pads adjacent to both of the longitudinal sidewalls of a rectangularly-shaped capacitor. Moreover, it is desirable to have the filter capacitor provide as much effective capacitance as a particular filter feedthrough assembly will afford.

SUMMARY OF THE INVENTION

The present invention relates to a hermetically sealed EMI filter feedthrough assembly for an active medical device that can be both implantable and intended to be worn externally. The novel active medical device comprises a feedthrough connected to an EMI filter capacitor, preferably with the capacitor having a square or rectangular shape, and with the filter capacitor only being terminated to an oxide-resistant system ground on one of its longitudinal sides. The opposed longitudinal side of the filter capacitor is terminated to an oxidized surface of the ferrule for the feedthrough. This opposite side oxidized connection considers the added expense attributed to providing gold contact pads adjacent to both of the longitudinal sidewalls of a rectangularly-shaped capacitor. Additionally, an opposite side oxidized connection helps stabilize the filter capacitor by preventing the capacitor from wobbling or rocking on the ferrule and insulator of the feedthrough.

Wobbling and rocking are particularly concerning when the filter capacitor is subjected to a high voltage surge such as occurs when an electrical pulse of several hundred volts passes through the capacitor during a cardiac defibrillation event, and the like. The resulting piezoelectric stress high voltage surge could cause the ceramic feedthrough capacitor to expand and contract which, if one side of the capacitor was not attached to the ferrule, could result in wobbling and rocking. Therefore, the present EMI filter capacitor having one side connected to an oxide-resistant system ground opposite a system ground to an oxidized surface offers a number of important manufacturing and cost reduction advantages as compared to the prior art EMI filter capacitor designs. Accordingly, this is a single sided low impedance system ground with a double-sided mechanical connection.

More particularly, the present invention relates to a hermetically sealed filtered feedthrough for an active medical device (AMD). In one embodiment, the filtered feedthrough comprises an electrically conductive ferrule having a ferrule opening extending to spaced-apart ferrule device and body fluid sides. The device side portions of the ferrule without a gold braze has an oxidized/oxidizable layer which can impede filter performance.

Preferably, the ferrule has a rectangular shape so that in a plan view looking at either of the ferrule device side or body fluid side, the ferrule comprises opposed ferrule first and second longitudinal side walls that extend to and meet with opposed ferrule third and fourth end walls with the longitudinal side walls being longer than the end walls. The first and second longitudinal side walls are aligned parallel to and on opposite sides of a ferrule center line that intersects the opposed third and fourth end walls.

Further, an electrically non-conductive insulator has an insulator outer surface that extends to spaced-apart insulator device and body fluid sides. The insulator disposed in the ferrule opening is hermetically sealed to the ferrule by a first gold braze so that when the ferrule hermetically sealed to the insulator is attached to an opening in a housing of an AMD, the ferrule and insulator body fluid sides, and the corresponding ferrule and insulator device sides reside outside and inside the AMD, respectively.

Still further, at least two insulator via holes extending to the insulator device and body fluid sides reside between the insulator second longitudinal side wall and the ferrule center line, and an insulator metallization is disposed on the insulator outer surface and in the insulator via holes. A respective one of at least two terminal pins reside in one of the insulator via holes where a second gold braze hermetically seals the terminal pin to the insulator. The terminal pins extend to terminal pin first and second ends with at least the terminal pin first ends extending outwardly beyond the insulator device side. That way, the at least two terminal pins reside between the insulator second longitudinal side wall and the ferrule center line.

The filtered feedthrough also comprises a filter feedthrough capacitor that is disposed at or adjacent to the insulator device side. The capacitor comprises a dielectric outer surface extending to a dielectric first major face spaced from a dielectric second major face. At least one active electrode plate and at least one ground electrode plate are supported in the capacitor dielectric in an interleaved, partially overlapping capacitive relationship. Then, at least two dielectric passageways extend to the dielectric first and second major faces and a capacitor internal metallization is disposed in the dielectric passageways. The at least one active electrode plate is connected to the capacitor internal metallization in the dielectric passageways, and the outwardly extending terminal pin first ends reside in a respective one of the dielectric passageways where the terminal pin is conductively connected to the capacitor internal metallization connected to the at least one active electrode plate by a first conductive material. Moreover, the at least one ground electrode plate is in a non-conductive relation with the capacitor internal metallization in the dielectric passageway.

A capacitor external metallization is disposed on a terminated first dielectric outer surface portion and on a spaced-apart terminated second dielectric outer surface portion of the dielectric outer surface. The at least one ground electrode plate is conductively connected to the capacitor external metallization at the terminated first and second dielectric outer surface portions with the at least one active electrode plate being in a non-conductive relation with the capacitor external metallization. A second conductive material connects the capacitor external metallization at the terminated first dielectric outer surface portion to the first gold braze sealing the insulator to the ferrule or to a gold bond pad supported on the ferrule device side, and a third conductive material connects the capacitor external metallization at the terminated second dielectric outer surface portion to the oxide layer on the ferrule device side.

These and other objects of the present invention will become increasingly more apparent to those skilled in the art by reference to the following description and to the appended drawings.

DETAILED DESCRIPTION OF THE PREFERRED EMBODIMENTS

Figure 1:
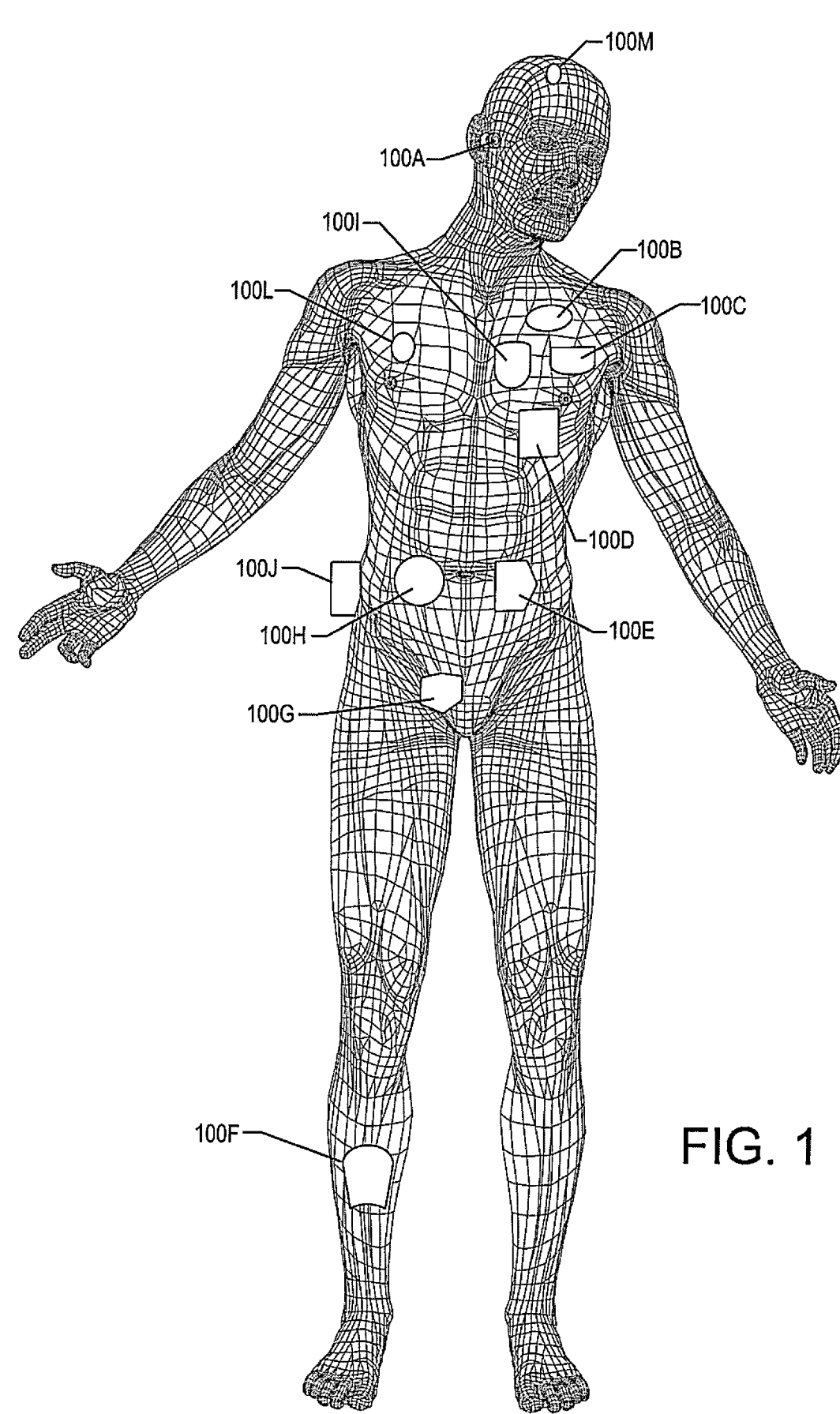
FIG. 1 is a wire formed diagram of a generic human body showing a number of medical devices 100A to 100L according to the present invention that can either be implanted in a patient's body tissue or attached externally to the body.
Figure 2:
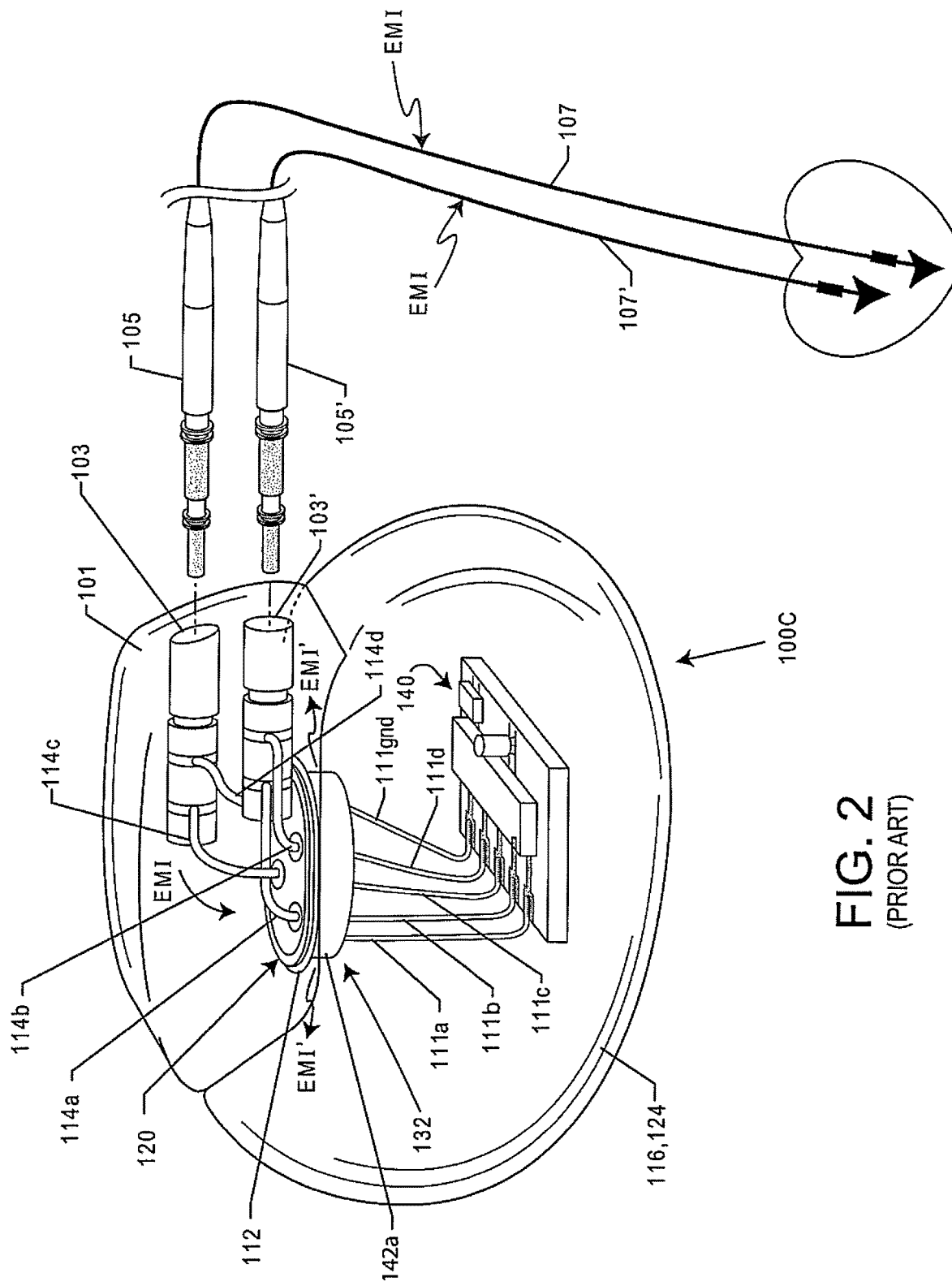
FIG. 2 is a side cutaway view of a prior art cardiac pacemaker 100C system.

Turning now to FIGS. 4 and 4A to 4C, these drawings illustrate an exemplary rectangularly-shaped EMI filter feedthrough assembly 210A having inline terminal pins as described in U.S. patent application Ser. No. 18/921,348, filed on Oct. 21, 2024, which is assigned to the assignee of the present invention and incorporated herein by reference. The filter feedthrough assembly 210A comprises an electrically conductive ferrule 112 having a ferrule opening extending to spaced-apart ferrule device and body fluid sides. Preferably, the ferrule 112 has a rectangular shape so that in a plan view, looking at either of the ferrule device or body fluid side, the ferrule comprises opposed ferrule first and second longitudinal sidewalls 112A and 112B that extend to and meet with opposed ferrule third and fourth end walls 112C and 112D. The longitudinal sidewalls 112A, 112B are longer than the end walls 112C, 112D and are aligned parallel to and on opposite sides of a ferrule center line (FIG. 4A) that intersects the opposed third and fourth end walls 112C, 112D.

The filter feedthrough assembly 210A further comprises an electrically non-conductive insulator 160, preferably made from alumina, having an insulator outer surface that extends to spaced-apart insulator device and body fluid sides. The insulator 160 is hermetically secured to the ferrule 112 in the ferrule opening by a first gold braze 150 that seals around the perimeter of the insulator. That way, when the ferrule 112 hermetically sealed to the insulator 160 is attached to an opening in a housing of any one of the above-described medical devices 100A to 100L, the ferrule and insulator body fluid sides, and the opposed ferrule and insulator device sides reside outside and inside the medical device, respectively.

Further, at least two, and preferably a plurality of, insulator via holes 126 extend to the insulator device and body fluid sides. Respective outer and inner insulator metallizations 151, 153 are disposed on the insulator outer surface and in the insulator via holes 126. These metallizations 151, 153 can be applied by sputtering, electroplating, physical vapor deposition or glass frit metallization bonding, and may comprise titanium, molybdenum, niobium, silver, copper, platinum, palladium, platinum silver, palladium silver, and combinations thereof.

Figure 4:
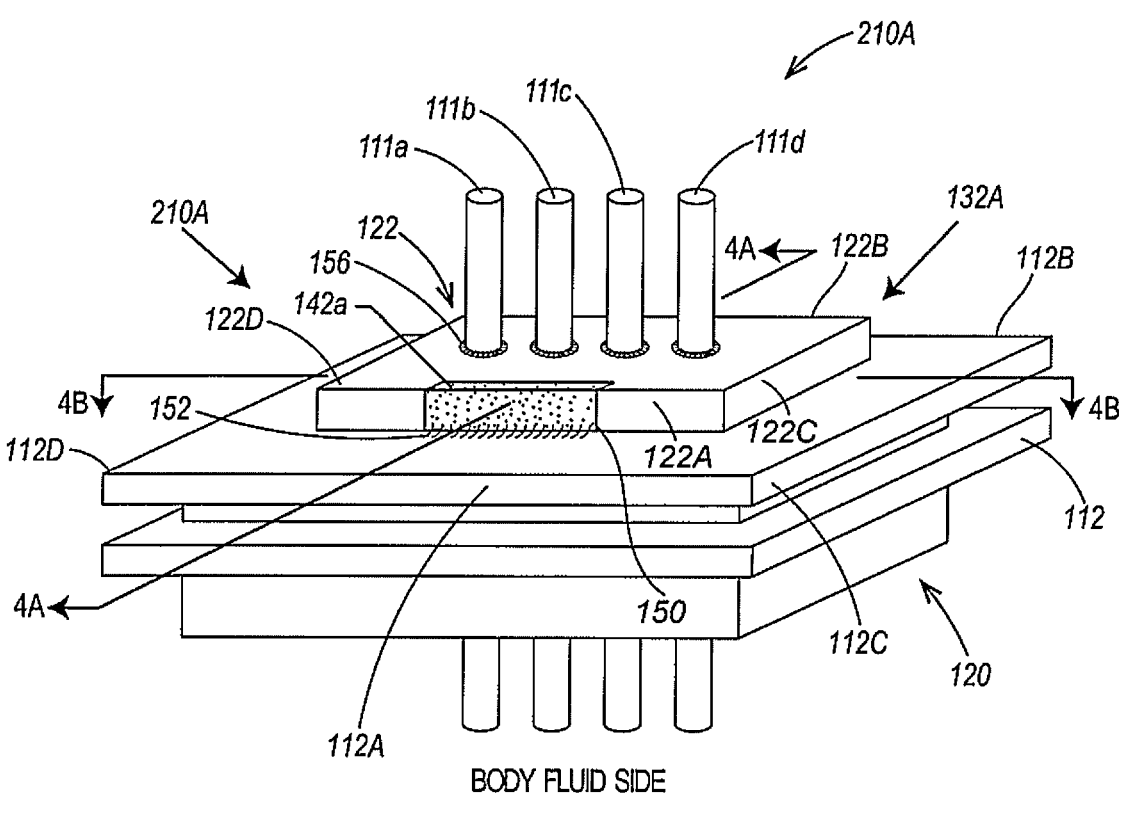
FIG. 4 is a perspective view of an inline quad-polar EMI filter feedthrough assembly 210A similar to that shown in FIG. 3 but with the back- or right-side 122B of the EMI filter capacitor 132A not being connected to an oxide-resistant ground on the ferrule 112 of the feedthrough 120.
Figure 4A:
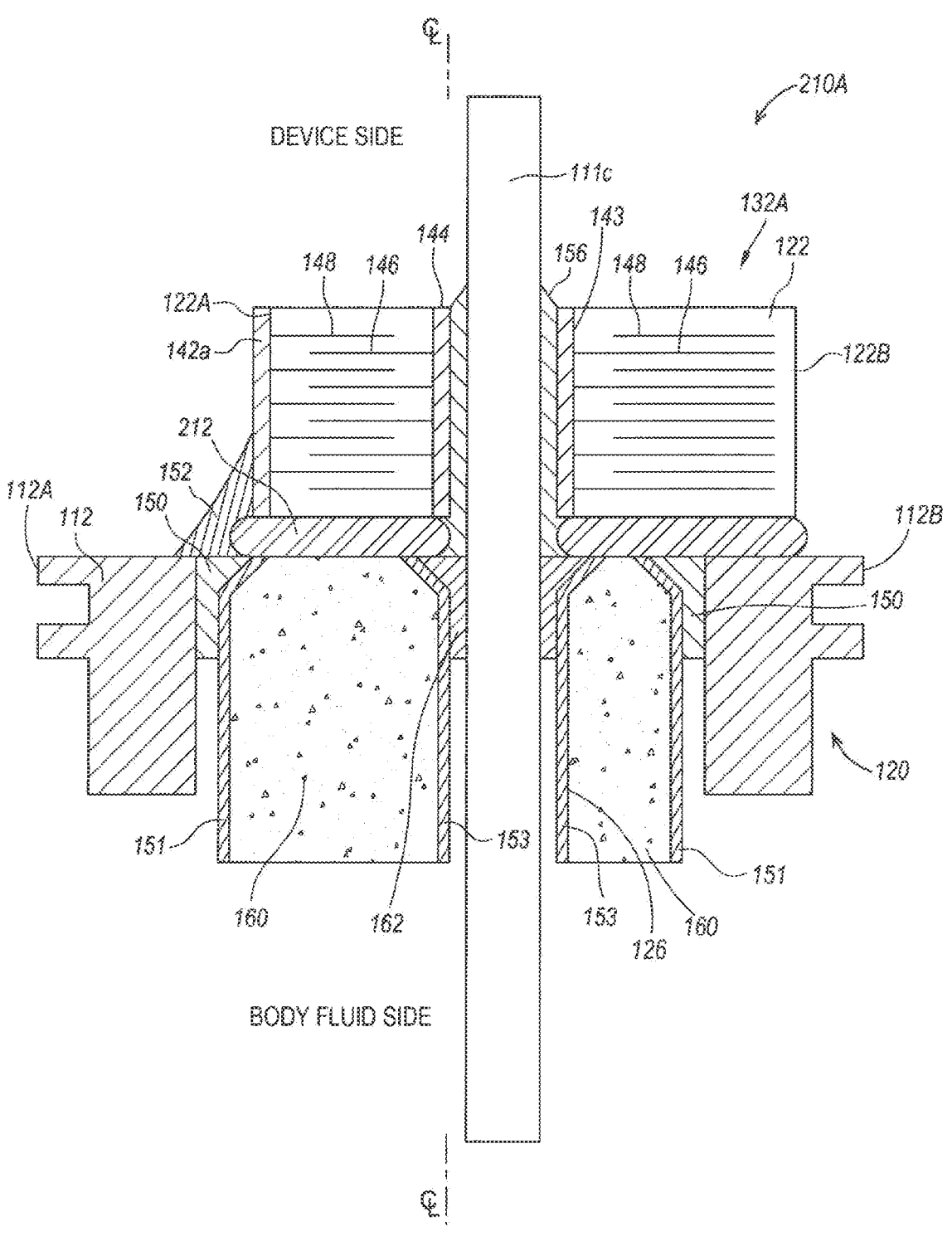
FIG. 4A is a cross-sectional view taken along line 4A-4A of FIG. 4.
Figure 4B:
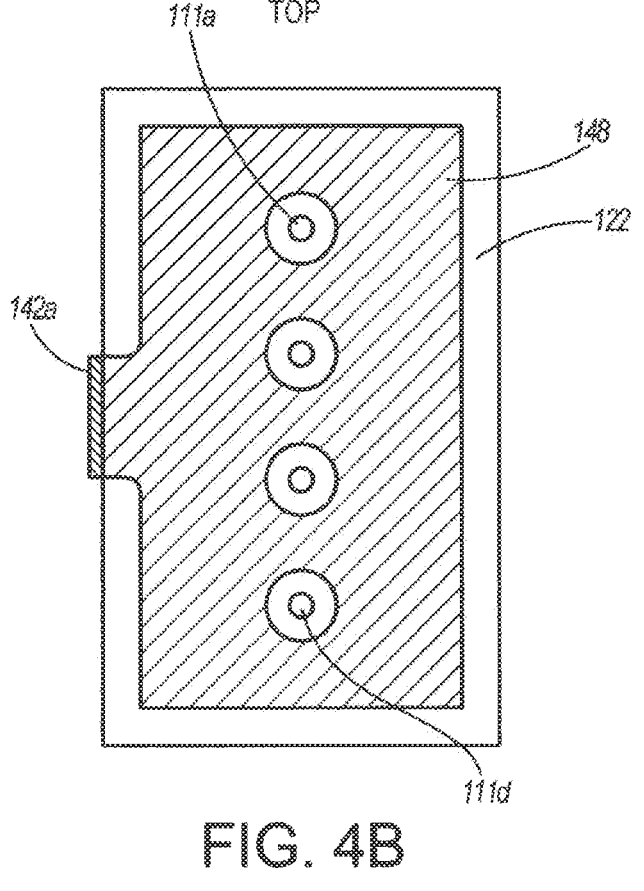
FIG. 4B is a cross-sectional view taken along line 4B-4B of FIG. 4.
Figure 4C:
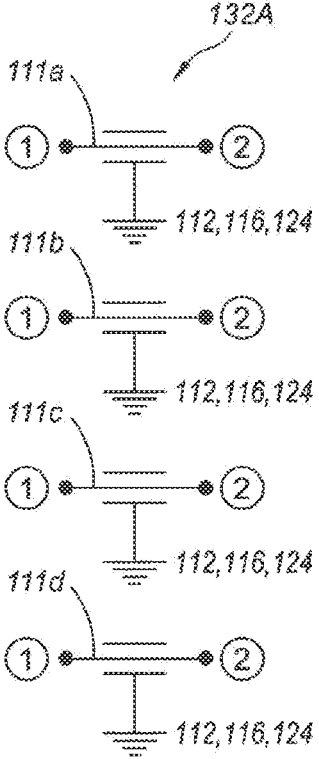
FIG. 4C is the electrical schematic of the quad-polar EMI filter capacitor shown in FIGS. 4, 4A and 4B.

A respective one of at least two, and preferably a plurality of, terminal pins (FIG. 4 shows an exemplary number of terminal pins 111a, 111b, 111c and 111d, known as a quadpolar filter) reside in one of the insulator via holes 126 where a second gold braze 162 hermetically seals the terminal pin to the inner metallization 153 contacted to the insulator 160 in the via hole 126. The terminal pins 111a, 111b, 111c and 111d extend to first and second ends with at least the terminal pin first ends extending outwardly beyond the insulator device side. The terminal pins reside between the ferrule second longitudinal sidewall 112B and the ferrule center line.

The filter feedthrough assembly 210A further comprises a filter capacitor 132A that is mounted adjacent to the insulator device side of the feedthrough 120. The filter capacitor 132A has a rectangularly-shaped or square-shaped, preferably rectangularly-shaped, dielectric 122 comprising an outer surface extending to a dielectric first major face spaced from a dielectric second major face. The capacitor dielectric 122 supports interleaved active and ground electrode plates 146 and 148. A plurality of inline passageways 143 extend through the dielectric 122. Each passageway 143 has an internal metallization 144. The metallized inline passageways 143 are electrically connected to the active electrode plates 146 but not to the ground electrode plates 148. An insulative washer 212 extending across the bottom of the EMI filter capacitor 132A rests on top of the device side of the ferrule 112 hermetically sealed to the insulator 160.

The rectangularly-shaped capacitor dielectric 122 has opposed relatively long longitudinal sides 122A and 122B that extend to and meet with relatively short ends 122C and 122D. An external metallization 142a is contacted to a terminated longitudinal side 122A but not to the opposite, unterminated longitudinal side 122B of the capacitor dielectric 122.

If desired, the opposed short ends 122C, 122D can also be terminated, but that is optional. In that case, the terminal pins and the ferrule are not centered between the longitudinal sides 122A and 122B of the capacitor dielectric 122. Instead, to increase capacitor design efficiency, the capacitor width is increased without increasing the overall size of the ferrule/hermetic seal, the terminal pins are deliberately offset toward the short side 122D. Effective capacitance area (ECA) is increased, which allows for a more conservative electrical design with improved capacitor reliability and production yields.

The ground electrode plates 148 extend to the external metallization 142a at the terminated longitudinal side 122A, but they do not extend to the opposed, unterminated longitudinal side 122B of the dielectric 122. The outwardly extending ends of a corresponding number of the inline terminal pins 111a, 111b, 111c and 111d comprising the feedthrough 120 are received in the dielectric passageways 143 where they are connected to the internal metallization 144 by an inner electrically conductive material 156. The inner conductive material 156 connects the metallized dielectric passageways 143 to the interleaved active electrode plates 146.

An outer conductive material 152 connects the capacitor external metallization 142a at the terminated longitudinal side 122A of the rectangularly-shaped dielectric 122 to a gold braze 150 that hermetically connects the insulator outer metallization 151 to the ferrule 112 comprising the previously described system ground 124. Contacting the outer conductive material 152 to the gold braze 150 provides a desirably very low impedance and very low resistance electrical connection. Suitable outer conductive materials 152 include a solder, a thermosetting electrically conductive adhesive, an electrically conductive silicone, a braze, an electrically conductive polyimide, an electrically conductive epoxy, and the like.

Calculations using PSpice and Microsim have demonstrated that there is sufficient insertion loss or filter attenuation to meet the needed performance requirements for MRI compatibility and compatibility with industry standard ISO14117 for all implantable cardiac electronic devices with only one side of a rectangularly-shaped EMI filter capacitor being connected to an oxide-resistant system ground, as shown in the filter feedthrough assembly illustrated in FIGS. 4 and 4A to 4C.

Figure 3:
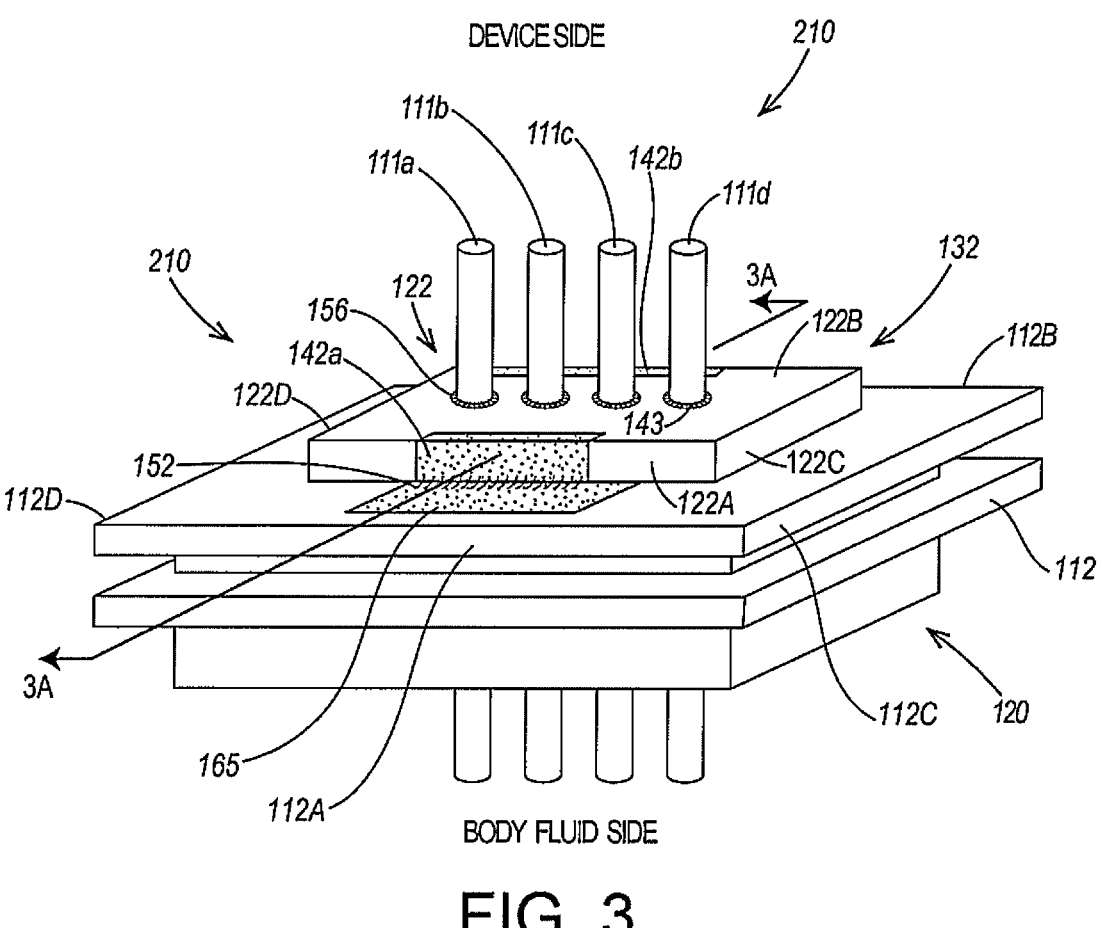
FIG. 3 is a perspective view of an inline quad-polar EMI filter feedthrough assembly 210 according to the prior art.
Figure 3A:
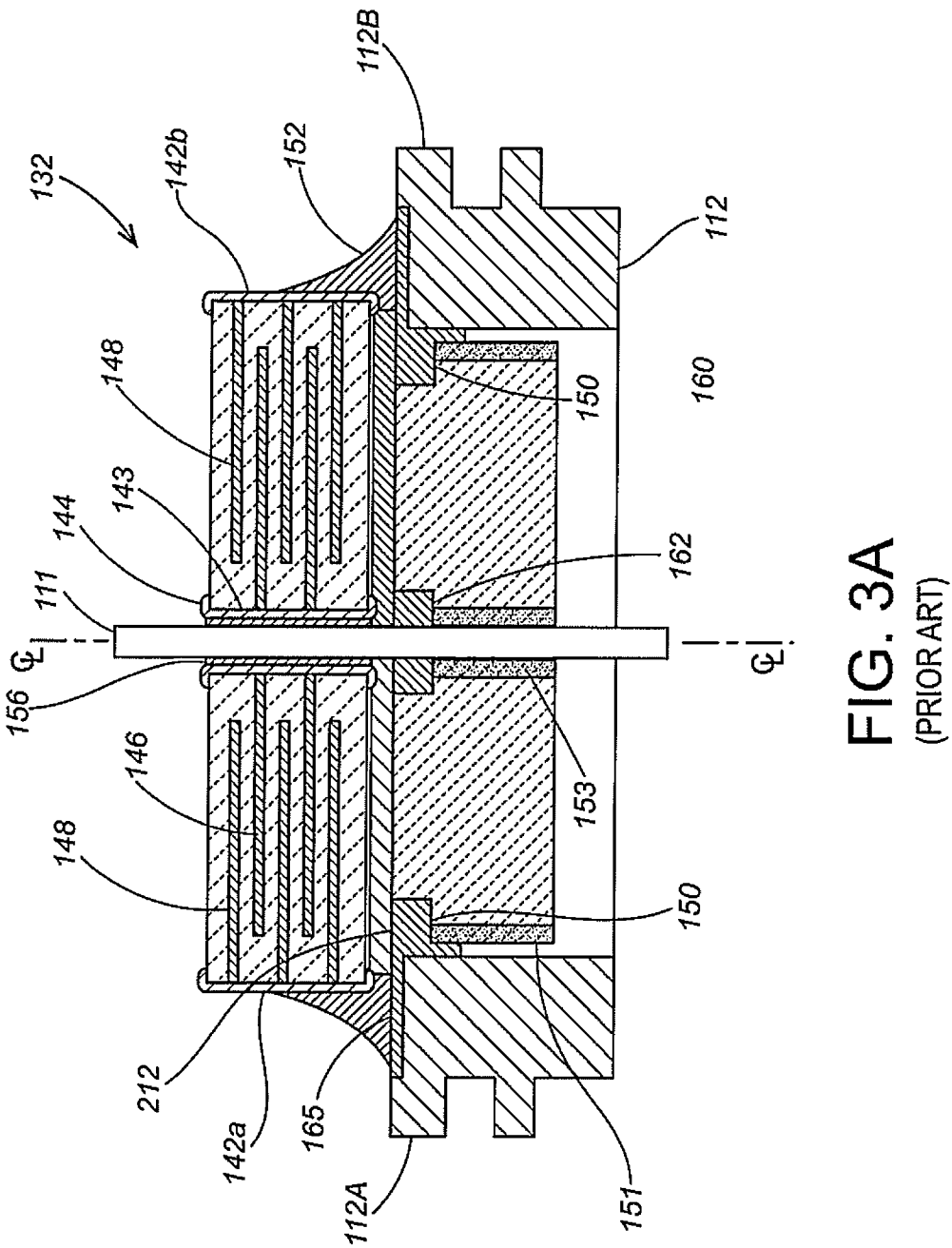
FIG. 3A is a cross-sectional view taken along line 3A-3A of FIG. 3.

However, there is a desire to further improve the stability of the filter feedthrough assembly illustrated in FIGS. 3 and 3A without adding too much extra cost. That is because wobbling and rocking of the EMI filter capacitor mounted to the device side of the feedthrough 120 are particularly concerning when the filter capacitor is subjected to a high voltage surge and piezoelectric stress such as occurs when an electrical pulse of several hundred volts passes through the capacitor during a cardiac defibrillation event, and the like.

Figure 5:
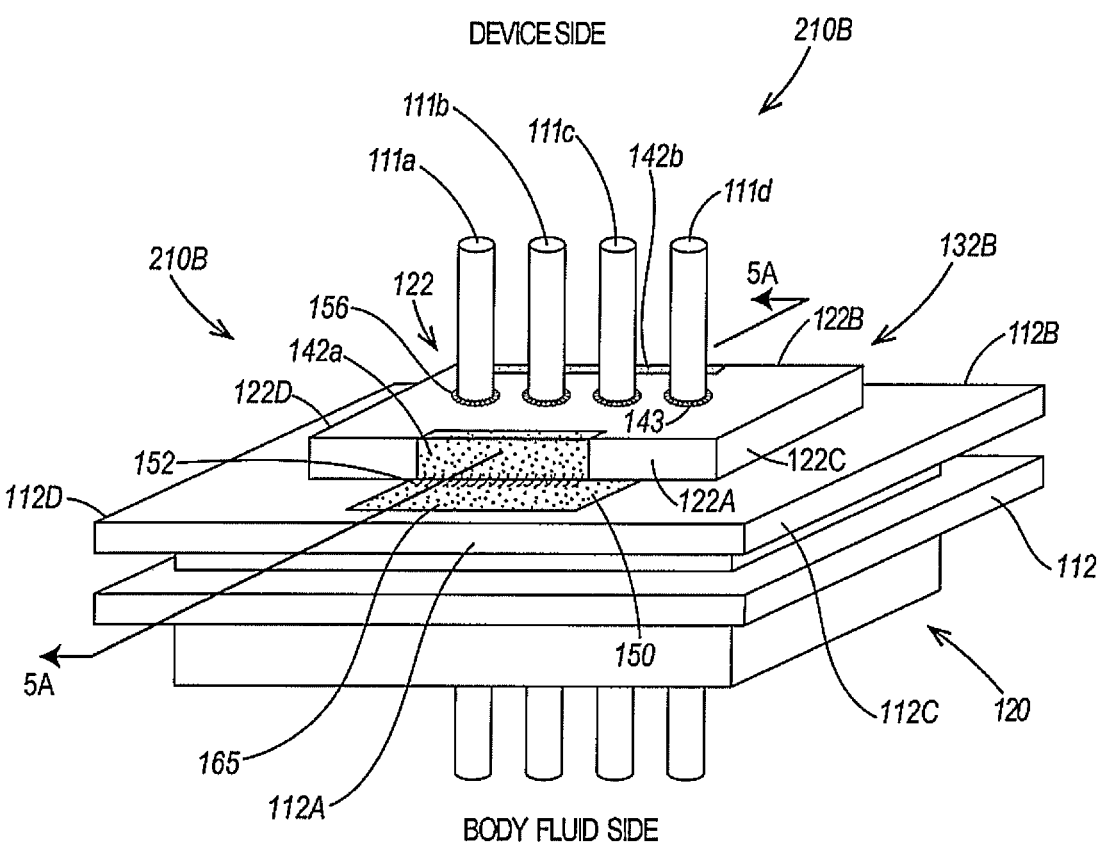
FIG. 5 is a perspective view of an inline quad-polar EMI filter feedthrough assembly 210B similar to that shown in FIG. 4 but with the front- or left-side 122A of the EMI filter capacitor 132B being connected to an oxide-resistant ground on the ferrule 112 and with the back- or right-side 122B of the filter capacitor 132B being connected to an oxidized surface of the ferrule 112 for the feedthrough 120.
Figure 5A:
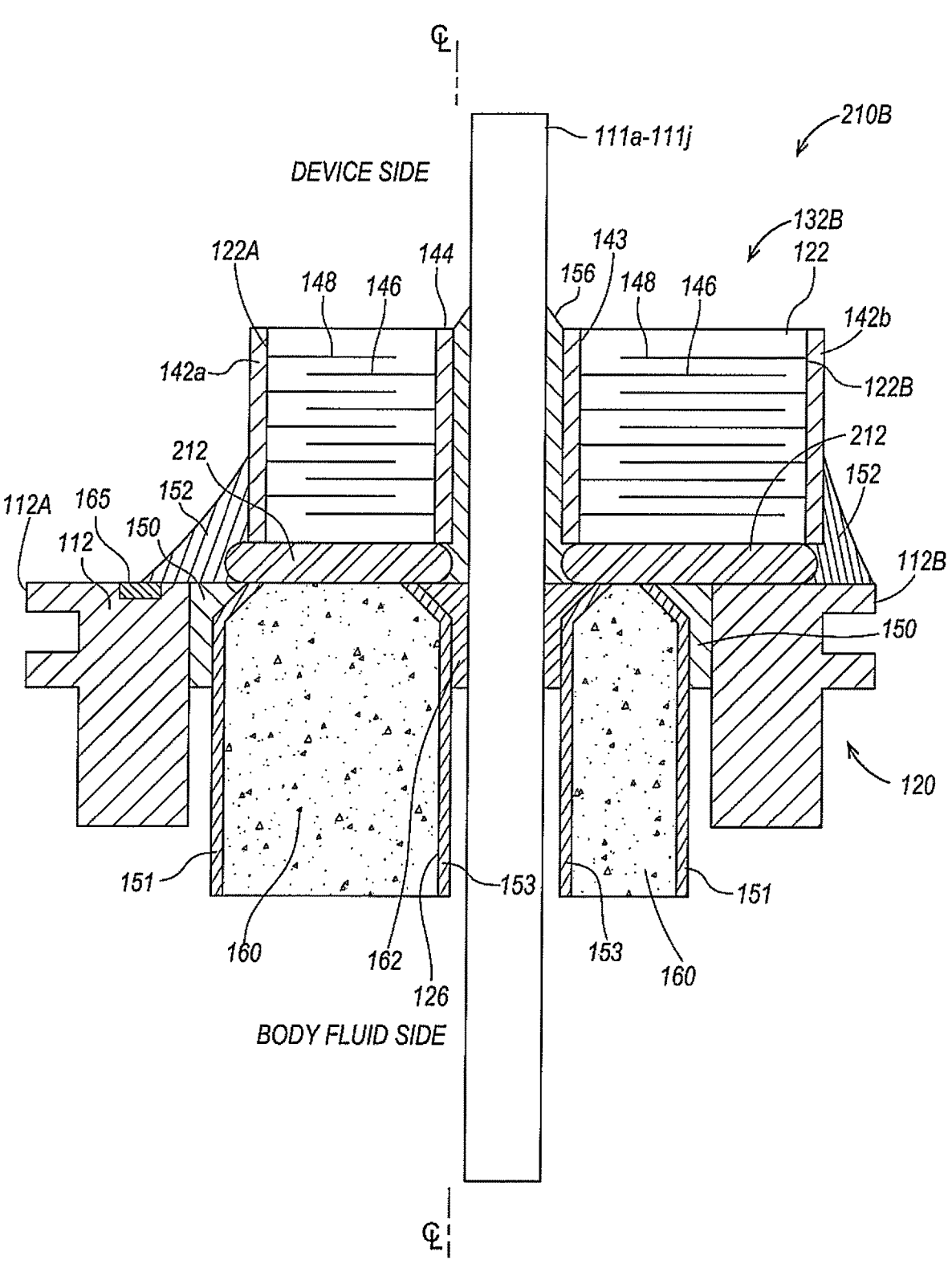
FIG. 5A is a cross-sectional view taken along line 5A-5A of FIG. 5 showing the terminal pins 111 being offset with respect to the center line of the ferrule and hermetic seal.
Figure 5B:
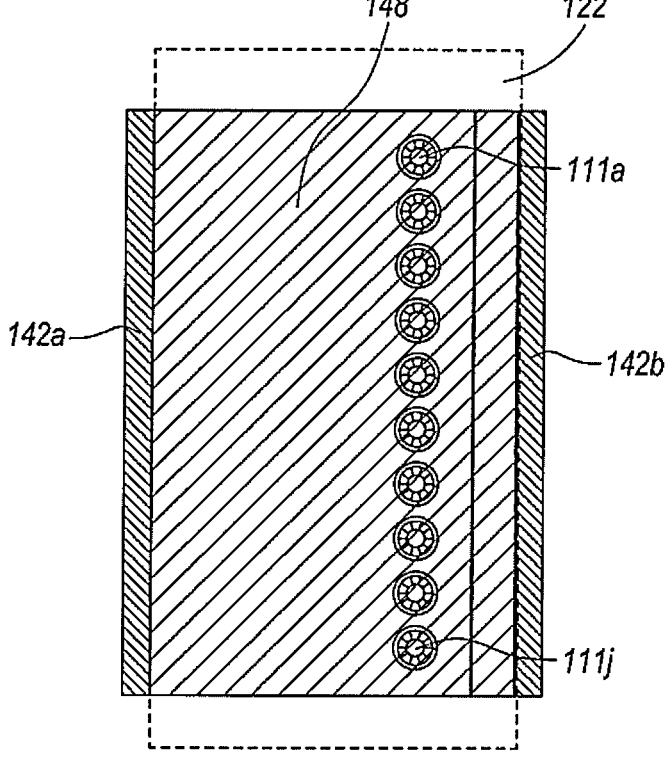
FIG. 5B is a cross-sectional view taken along a ground electrode plate 148 for the filter feedthrough assembly 210B similar to that shown in FIG. 5 but with the terminal pins 111a to 111j being offset closer to the back- or right-side 122B of the filter capacitor 132B connected to an oxidized surface of the ferrule 112 than to the front- or left-side 122A of the EMI filter capacitor 132B connected to an oxide-resistant ground on the ferrule 112 for the feedthrough 120.

Turning now to FIGS. 5, 5A and 5B, a filter feedthrough assembly 210B according to the present invention is illustrated. The filter feedthrough assembly 210B comprises a filter capacitor 132B having one side electrically connected to an oxide-resistant system ground (gold braze 150) opposite a system ground to an oxidized surface. Not only does this construction offers a number of important manufacturing and cost reduction advantages as compared to the filter feedthrough assembly 210A illustrated in FIGS. 4 and 4A to 4C but connecting the opposite side 122B of the capacitor dielectric 122 to an oxidized surface of the ferrule 112 helps to mechanically stabilize the filter capacitor by preventing the capacitor from wobbling or rocking on the feedthrough, particularly during a high voltage discharge event. In that respect, an electrically conductive connection 152 is made to the gold braze 150 adjacent to side 122A but also to the oxidized ferrule surface on the 122B side. The oxidized surface on the 122B side still allows for some reduced filter performance, but this is a positive, not a negative (something is better than nothing). The downside is that additional expense is incurred by adding ground metallization 142b connected to capacitor ground electrode plates 148.

In particular, the FIGS. 5, 5A and 5B illustrate an exemplary rectangularly-shaped EMI filter feedthrough assembly 210B comprising an electrically conductive ferrule 112 having a ferrule opening extending to spaced-apart ferrule device and body fluid sides. Preferably, the ferrule 112 has a rectangular shape so that in a plan view, looking at either of the ferrule device or body fluid side, the ferrule comprises opposed ferrule first and second longitudinal sidewalls 112A and 112B that extend to and meet with opposed ferrule third and fourth end walls 112C and 112D with the longitudinal sidewalls 112A, 112B being longer than the end walls 112C, 112D. The first and second longitudinal sidewalls 112A, 112B are aligned parallel to and on opposite sides of a ferrule center line that intersects the opposed third and fourth end walls 112C, 112D.

The filter feedthrough assembly 210B further comprises an electrically non-conductive insulator 160, preferably made from alumina, having an insulator outer surface that extends to spaced-apart insulator device and body fluid sides. The insulator 160 is hermetically sealed to the ferrule 112 in the ferrule opening by a first gold braze 150 that seals around the perimeter of the insulator. That way, when the ferrule 112 hermetically sealed to the insulator 160 is attached to an opening in a housing of any one of the above-described medical devices 100A to 100L, the ferrule and insulator body fluid sides, and the opposed ferrule and insulator device sides reside outside and inside the medical device, respectively.

Further, at least two, and preferably a plurality of, insulator via holes 126 extend to the insulator device and body fluid sides. Respective insulator outer and inner metallizations 151, 153 are disposed on the insulator outer surface and in the insulator via holes 126. These metallizations 151, 153 can be applied by sputtering, electroplating, physical vapor deposition or glass frit metallization bonding, and may comprise titanium, molybdenum, niobium, silver, copper, platinum, palladium, platinum silver, palladium silver, and combinations thereof.

A respective one of at least two, and preferably a plurality of, terminal pins (FIG. 5 shows an exemplary number of terminal pins 11a, 11b, 11c and 111d while FIG. 5B shows ten exemplary terminal pins 111a to 111j) reside in one of the insulator via holes 126 where a second gold braze 162 hermetically seals the terminal pin to the inner metallization 153 contacted to the insulator 160 in the via hole. The terminal pins 111a to 111d or 111a to 111j extend to terminal pin first and second ends with at least the terminal pin first ends extending outwardly beyond the insulator device side.

The filter feedthrough assembly 210B further comprises the filter capacitor 132B that is mounted adjacent to the insulator device side of the feedthrough 120 and that comprises a rectangularly-shaped or square-shaped, preferably rectangularly-shaped, dielectric 122 supporting interleaved active and ground electrode plates 146 and 148. A plurality of inline passageways 143 extend through the dielectric 122. Each of the inline passageways 143 has an internal metallization 144. The metallized inline passageways 143 are electrically connected to the active electrode plates 146 but not to the ground electrode plates 148. An insulative washer 212 extending across the bottom of the EMI filter capacitor 132B rests on top of the device side of the ferrule 112 hermetically sealed to the insulator 160.

The rectangularly-shaped dielectric 122 has opposed relatively long longitudinal sides 122A and 122B that extend to and meet with relatively short ends 122C and 122D. Respective external metallizations 142a, 142b are contacted to the opposed terminated longitudinal sides 122A and 122B of the capacitor dielectric 122. Desirably, the opposed short ends 122C, 122D are not terminated. In the alternative, the opposed short ends 122C, 122D can be terminated, but little in filter performance is gained at added expense.

The ground electrode plates 148 extend to the external metallization 142a at the longitudinal side 122A and to the external metallization 142b at the opposed longitudinal side 122B of the dielectric 122. The outwardly extending ends of a corresponding number of the inline terminal pins 111a to 111d or 111a to 111j comprising the feedthrough 120 are received in the dielectric passageways 143 where they are connected to the internal metallization 144 by an inner electrically conductive material 156. The inner conductive material 156 connects the metallized dielectric passageways 143 to the interleaved active electrode plates 146.

An outer conductive material 152 connects the capacitor external metallization 142a at the terminated longitudinal side 122A of the rectangularly-shaped dielectric 122 to a gold braze 150 that hermetically connects the insulator outer metallization 151 to the ferrule 112 comprising the previously described system ground 124. If desired, an oxide-resistant material 165, preferably gold, in the form of a contact pad is supported on the device side surface of the ferrule 112 adjacent to the gold braze 150. The contact pad 165 can be continuous with the gold braze 150 or the braze 150 and pad 165 can be spaced from each other by a portion of the ferrule 112 (FIG. 5A). Preferably, the outer conductive material 152 is contacted to the gold braze 150 and, if present, to the gold contact pad 165 to provide a desirably very low impedance and very low resistance electrical connection.

As previously described, the ferrule 112 is preferably made from titanium. Titanium has excellent corrosion resistance and biocompatibility. However, in the presence of human body fluids, the excellent corrosion resistance exhibited by titanium is due to the formation of a thermodynamically stable, continuous, highly adherent, and protective surface oxide film. Since titanium metal is highly reactive and has an extremely high affinity for oxygen, this surface oxide film is formed spontaneously and instantly when a fresh titanium metal surface is exposed to air and moisture (even at room temperature). Unfortunately, the titanium oxide layer acts as an insulator that impedes proper filter bypass performance.

Nonetheless, for improved stability of the EMI filter capacitor mounted to the feedthrough 120, the outer conductive material 152 also connects the capacitor external metallization 142b at the terminated longitudinal side 122B of the rectangularly-shaped dielectric 122 to the device side surface of the ferrule 112. Since gold is a relatively expensive material, this connection of the capacitor external metallization 142*b* at the terminated longitudinal side 122B is spaced outwardly from the gold braze 150 that hermetically connects the insulator outer metallization 151 to the ferrule 112 comprising the previously described system ground 124. However, to save the added expense of an oxide-resistant connection adjacent to the terminated longitudinal side 122B of the rectangularly-shaped dielectric 122, a gold contact pad is not provided adjacent to the capacitor external metallization 142*b*. Again, suitable outer conductive materials 152 for connection to both capacitor metallizations 142*a*, 142*b* include a solder, a thermosetting electrically conductive adhesive, an electrically conductive silicone, a braze, an electrically conductive polyimide, an electrically conductive epoxy, and the like.

Figure 3B:
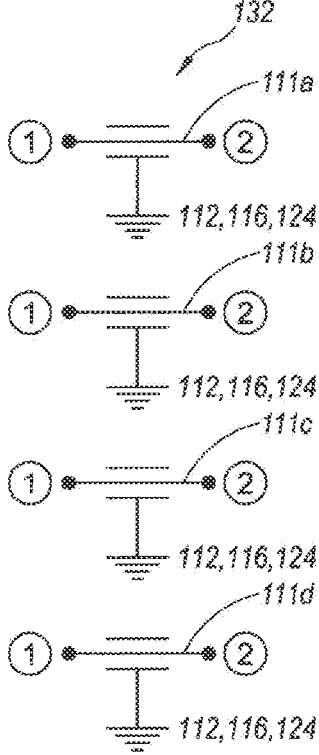
FIG. 3B is the electrical schematic of the quad-polar EMI filter capacitor shown in FIGS. 3 and 3A.

While this embodiment of an EMI filter feedthrough assembly 210B according to the present invention does not exhibit the same level of insertion loss or filter attenuation as is exhibited by the filter feedthrough assembly 210 illustrated in FIGS. 3, 3A and 3B and by the filter feedthrough assembly 210A illustrated in FIGS. 4 and 4A to 4C, calculations using PSpice and Microsim and insertion loss measurements in dB have demonstrated that there is sufficient insertion loss or filter attenuation to meet the needed performance requirements for MRI compatibility for the various medical devices 100A to 100L described above.

Moreover, for improved structural integrity, it is an aspect of the filter feedthrough assembly 210B according to the present invention that the opposed terminated longitudinal side 122B of an EMI filter capacitor, preferably a square-shaped or rectangularly-shaped capacitor, is connected to the oxidized device side surface of the ferrule. Since contacting an oxide-resistant material, for example, gold, to the device side surface of the ferrule adjacent to the both of the longitudinal sides 122A and 122B of the capacitor dielectric 122 represents an additional expense in gold as a noble precious metal, according to the present invention, only one of the longitudinal sides 122A or 122B is contacted to an oxide-resistant surface. The other of the sides 122A and 122B in not contacted to an oxide resistant surface. While not optimum, the improved structural integrity for the filter feedthrough assembly 210B is a viable tradeoff.

In that respect, for a square-shaped or rectangularly-shaped filter capacitor, the longitudinal side of the capacitor that is opposite the terminated longitudinal side connected to the oxide-resistant gold braze, and optionally to the gold pad 165, on the device side surface of the ferrule is also connected to the ferrule 112, but this side of the ferrule has an oxidized surface at the connection. In other words, according to the present invention, it is not necessary that this opposed ground termination is connected to a low impedance non-oxidizable surface, such as gold.

Figure 6:
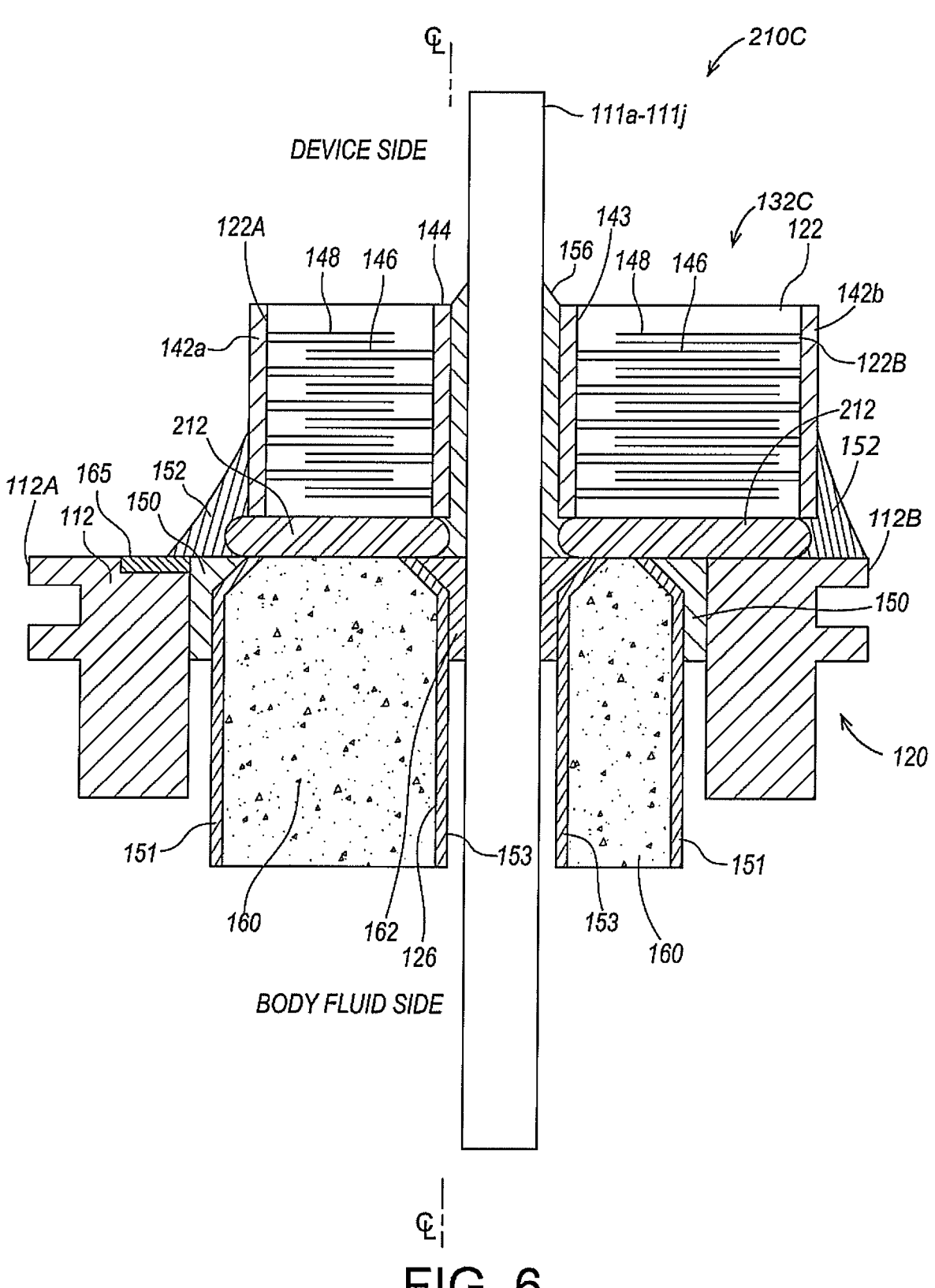
FIG. 6 is a cross-sectional view of an EMI filter feedthrough assembly 210C similar to the EMI filter feedthrough assembly 210B shown in FIGS. 5, 5A and 5B except that the capacitor dielectric 122 supports dual active and ground electrode plates 146, 148.

The filter feedthrough assembly 210C illustrated FIG. 6 is similar to the assembly 210*b* shown in FIG. 5 except that the active and ground electrode plates 146 and 148 now occur in electrode plate pairs. These are known as dual electrodes. Dual electrodes are thoroughly described in U.S. Pat. No. 5,978,204 (Ex Parte Reexamination Certificate 4920*th*), which is assigned to the assignee of the present invention and herein fully incorporated by reference. In the present invention, dual electrodes are very important in that the electrode total conductive area is greatly increased. This more than makes up for the ground 142*b* on the right-hand side of the filtered filter capacitor being directly connected to an oxidized surface of the ferrule 112. The dual electrodes have a very low equivalent series resistance and a very low impedance across the width of the feedthrough filter capacitor 132C. It is therefore a preferred embodiment of the present invention that the electrodes be in dual electrode pairs.

One might ask why not three or four electrodes in parallel, and the answer is that no more than dual electrodes will work. The addition of a third electrode between a pair of dual electrodes would do nothing since there is no electric field between the third electrode and its adjacent electrode plates.

Thus, the present invention relates to a filter feedthrough assembly comprising a square- or rectangularly-shaped EMI filter capacitor. The feedthrough comprises an insulator sealed in a ferrule opening. A terminal pin sealed in an insulator via hole has a first end that extends outwardly beyond an insulator device side. The square- or rectangularly-shaped EMI filter capacitor is positioned adjacent to the insulator device side and comprises a dielectric supporting interleaved active and ground electrode plates. At least one passageway extending through the dielectric has an internal metallization. An external metallization is contacted to the opposed longitudinal sides of the square- or rectangularly-shaped capacitor dielectric. The capacitor ground electrode plates extend to the external metallizations at the terminated longitudinal sides. The outwardly extending terminal pin end is connected to the internal metallization in the dielectric passageway which in turn is connected to the active electrode plates. A conductive material connects the external metallization contacted to one of the longitudinal sides to an oxide-resistant material supported on the device side of the ferrule while the external metallization contacted to the other longitudinal side of the capacitor dielectric is connected to an oxidized surface of the ferrule.

It is appreciated that various modifications to the inventive concepts described herein may be apparent to those skilled in the art without departing from the spirit and scope of the present invention as defined by the hereinafter appended claims.

What is claimed is:

1. A hermetically sealed EMI filtered feedthrough for an active medical device (AMD), the EMI filtered feedthrough comprising:
   a titanium ferrule comprising a ferrule opening extending to a ferrule device side spaced from a ferrule body fluid side, wherein at least a portion of the ferrule device side has an exposed layer of titanium oxide;
   b) an electrically non-conductive insulator comprising an insulator outer surface extending to an insulator device side spaced from an insulator body fluid side, wherein the insulator is hermetically sealed to the ferrule in the ferrule opening by a first gold braze so that when the ferrule is attached to an opening in a housing of an AMD, the ferrule and insulator body fluid sides, and the ferrule and insulator device sides reside outside and inside the AMD, respectively, and wherein at least two insulator via holes extend to the insulator device and body fluid sides;
   c) an insulator internal metallization disposed in the at least two insulator via holes;
   d) first and second terminal pins residing in a respective one of the at least two insulator via holes where a second gold braze hermetically seals the terminal pin to the insulator internal metallization, wherein the first and second terminal pins extend to first and second terminal pin first ends spaced from first and second terminal pin second ends, and wherein at least the first and second terminal pin first ends extend outwardly beyond the insulator device side;

e) a filter capacitor disposed at or adjacent to the insulator device side, the filter capacitor comprising:

i) a capacitor dielectric comprising a dielectric outer surface extending to a dielectric first major face spaced from a dielectric second major face;

ii) at least one active electrode plate and at least one ground electrode plate supported in the capacitor dielectric in an interleaved, partially overlapping capacitive relationship;

iii) first and second dielectric passageways extending into the capacitor dielectric from the dielectric first major face adjacent to the insulator device side;

iv) a capacitor internal metallization disposed in the first and second dielectric passageways and being conductively connected to the at least one active electrode plate, wherein the outwardly extending first and second terminal pin first ends reside in the respective first and second dielectric passageways where the terminal pins are conductively connected to the capacitor internal metallization connected to the at least one active electrode plate by a first conductive material; and v) a capacitor external metallization disposed on a terminated first dielectric outer surface portion and on a spaced-apart terminated second dielectric outer surface portion of the dielectric outer surface, wherein the at least one ground electrode plate is conductively connected to the capacitor external metallization at the terminated first and second dielectric outer surface portions; and f) a second conductive material connecting the capacitor external metallization at the terminated first dielectric outer surface portion to the first gold braze sealing the insulator to the ferrule; and g) a third conductive material connecting the capacitor external metallization at the terminated second dielectric outer surface portion to the exposed layer of titanium oxide on the ferrule device side, spaced outwardly beyond the first gold braze, wherein the third conductive material does not contact the first gold braze sealing the insulator to the ferrule.

2. The EMI filtered feedthrough of claim 1, wherein the at least one active electrode plate comprises a closely spaced pair of active electrode plates and the at least one ground electrode plate comprises a closely-spaced pair of ground electrode plates.

3. The EMI filtered feedthrough of claim 1, wherein an insulative washer is disposed between the insulator and the filter capacitor.

4. The EMI filtered feedthrough of claim 1, wherein the ferrule is configured to be attachable to a housing of an active e medical device by a laser weld.

5. The EMI filtered feedthrough of claim 1, wherein the ferrule is a continuous part of an active medical device housing.

6. The EMI filtered feedthrough of claim 1, wherein spaced-apart unterminated third and fourth dielectric outer surface portions of the capacitor dielectric reside between and electrically isolate the terminated first and second dielectric outer surface portions from each other.

7. The EMI filtered feedthrough of claim 6, wherein, in a plan view looking at the dielectric first major face, the capacitor dielectric has a rectangular shape comprising opposed dielectric first and second long sides extending to and meeting with opposed dielectric third and fourth short ends, and wherein the at least one ground electrode plate extends to the dielectric first and second long sides comprising the spaced-apart terminated first and second dielectric outer surface portions, but the ground electrode plate does not extend to the dielectric third and fourth short ends comprising the unterminated third and fourth dielectric outer surface portions of the capacitor dielectric.

8. The EMI filtered feedthrough of claim 6, wherein, in a plan view looking at the dielectric first major face, the capacitor dielectric has a square shape comprising opposed dielectric first and second sides extending to and meeting with opposed dielectric third and fourth sides, the dielectric first and second sides being substantially equal in length to the dielectric third and fourth sides, and wherein the at least one ground electrode plate extends to the spaced-apart dielectric first and second sides comprising the spaced-apart terminated first and second dielectric outer surface portions, but the ground electrode plate does not extend to the dielectric third and fourth sides comprising the unterminated third and fourth dielectric outer surface portions of the capacitor dielectric.

9. The EMI filtered feedthrough of claim 1, wherein, in a plan view looking at the ferrule device side:

a) the ferrule has a rectangular shape comprising ferrule first and second longitudinal sidewalls that extend to and meet with opposed ferrule third and fourth end walls, wherein the ferrule first and second longitudinal sidewalls are aligned parallel to and on opposite sides of a ferrule center line that bisects the opposed ferrule third and fourth end walls;

b) the insulator hermetically sealed to the ferrule in the ferrule opening has opposed insulator first and second longitudinal sidewalls that extend to and meet with opposed insulator third and fourth end walls so that the shape of the insulator matches the shape of the ferrule opening, and c) the first and second terminal pins residing in a respective one of the at least two insulator via holes reside between the insulator second longitudinal sidewall and the ferrule center line.

10. The EMI filtered feedthrough of claim 9, wherein the first and second terminal pins residing in a respective one of the at least two insulator via holes are aligned parallel to the insulator second longitudinal sidewall and the ferrule center line.

11. The EMI filtered feedthrough of claim 1, further comprising a gold bond pad supported on the ferrule device side, wherein the second conductive material connects the capacitor external metallization at the terminated first dielectric outer surface portion to at least one of the first gold braze sealing the insulator to the ferrule and the gold bond pad supported on the ferrule device side.

12. The EMI filtered feedthrough of claim 11, wherein the gold bond pad is spaced outwardly from the first gold braze sealing the insulator to the ferrule.

13. The EMI filtered feedthrough of claim 11, wherein the first conductive material conductively connecting the outwardly extending first and second terminal pin first ends to the capacitor internal metallization connected to the at least one active electrode plate, the second conductive material connecting the capacitor external metallization at the terminated first dielectric outer surface portion to at least one of the first gold braze or the gold bond pad supported on the ferrule device side, and the third conductive material connecting the capacitor external metallization at the terminated second dielectric outer surface portion to the ferrule device side are individually selected from the group of a solder, a thermosetting electrically conductive adhesive, an electrically conductive silicone, a braze, an electrically conductive polyimide, and an electrically conductive epoxy.

14. A hermetically sealed EMI filtered feedthrough for an active medical device (AMD), the EMI filtered feedthrough comprising;

a) a titanium ferrule comprising a ferrule opening extending to a ferrule device side spaced from a ferrule body fluid side, wherein at least a portion of the ferrule device side has an exposed layer of titanium oxide;

b) a gold bond pad supported on the ferrule device side;

c) an electrically non-conductive insulator comprising an insulator outer surface extending to an insulator device side spaced from an insulator body fluid side, wherein the insulator is hermetically sealed to the ferrule in the ferrule opening by a first gold braze so that when the ferrule is attached to an opening in a housing of an AMD, the ferrule and insulator body fluid sides, and the ferrule and insulator device sides reside outside and inside the AMD, respectively, and wherein at least two insulator via holes extend to the insulator device and body fluid sides;

d) an insulator internal metallization disposed in the at least two insulator via holes;

e) first and second terminal pins residing in a respective one of the at least two insulator via holes where a second gold braze hermetically seals the terminal pin to the insulator internal metallization, wherein the first and second terminal pins extend to first and second terminal pin first ends spaced from first and second terminal pin second ends, and wherein at least the first and second terminal pin first ends extend outwardly beyond the insulator device side;

f) a filter capacitor disposed at or adjacent to the insulator device side, the filter capacitor comprising:

i) a capacitor dielectric comprising a dielectric outer surface extending to a dielectric first major face spaced from a dielectric second major face;

ii) at least one active electrode plate and at least one ground electrode plate supported in the capacitor dielectric in an interleaved, partially overlapping capacitive relationship;

iii) first and second dielectric passageways extending into the capacitor dielectric from the dielectric first major face adjacent to the insulator device side;

iv) a capacitor internal metallization disposed in the first and second dielectric passageways and being conductively connected to the at least one active electrode plate, wherein the outwardly extending first and second terminal pin first ends reside in the respective first and second dielectric passageways where the terminal pins are conductively connected to the capacitor internal metallization connected to the at least one active electrode plate by a first conductive material; and v) a capacitor external metallization disposed on a terminated first dielectric outer surface portion and on a spaced-apart terminated second dielectric outer surface portion of the dielectric outer Surface, wherein the terminated first dielectric outer surface portion resides spaced above the first gold braze hermetically sealing the insulator to the ferrule, and the terminated second dielectric outer surface portion extends outwardly beyond the first gold braze, and wherein the at least one ground electrode plate is conductively connected to the capacitor external metallization at the terminated first and second dielectric outer surface portions; and g) a second conductive material connecting the capacitor external metallization at the terminated first dielectric outer surface portion to at least one of the first gold braze sealing the insulator to the ferrule or the gold bond pad supported on the ferrule device side; and h) a third conductive material connecting the capacitor external metallization at the terminated second dielectric outer surface portion to the exposed layer of titanium oxide on the ferrule device side, spaced outwardly beyond the first gold braze, wherein the third conductive material does not contact the first gold braze sealing the insulator to the ferrule or the gold bond pad supported on the ferrule device side.

15. The EMI filtered feedthrough of claim 14, wherein;

a) the ferrule comprises opposed ferrule first and second longitudinal sidewalls that extend to and meet with opposed ferrule third and fourth end walls, the ferrule first and second longitudinal sidewalls being aligned parallel to and on opposite sides of a ferrule center line that bisects the opposed ferrule third and fourth end walls;

b) the insulator hermetically sealed to the ferrule in the ferrule opening has opposed insulator first and second longitudinal sidewalls that extend to and meet with opposed insulator third and fourth end walls with the at least two insulator via holes residing between the insulator second longitudinal sidewall and the ferrule center line;

c) the filter capacitor has a rectangular shape so that in & plan view looking at the dielectric first major face, opposed dielectric first and second long sides extend to and meet with opposed dielectric third and fourth short ends;

d) the at least one ground electrode plate is conductively connected to the capacitor external metallization disposed on the dielectric first and second long sides as the terminated first and second dielectric outer surface portions;

e) the dielectric first long side resides spaced above the first gold braze or the gold bond pad supported on the ferrule device side, and the dielectric second long side extends laterally outwardly beyond the first gold braze; and f) the second conductive material conductively connects the capacitor external metallization at the dielectric first long side serving as the terminated first dielectric outer surface portion to at least one of the first gold braze or the gold bond pad, and the third conductive material conductively connects the capacitor external metallization at the terminated second dielectric outer surface portion to the exposed layer of titanium oxide on the ferrule device side, spaced outwardly beyond the first gold braze, wherein the third conductive material does not contact the first gold braze sealing the insulator to the ferrule or the gold bond pad supported on the ferrule device side.

16. The EMI filtered feedthrough of claim 14, wherein the gold bond pad is spaced outwardly from the first gold braze sealing the insulator to the ferrule.

17. A hermetically sealed BMI filtered feedthrough for an active implantable medical device (AMD), the EMI filtered feedthrough comprising:

a) a titanium ferrule comprising a ferrule opening extending to a ferrule device side spaced from a ferrule body fluid side, wherein at least a portion of the ferrule device side has an exposed layer of titanium oxide;

b) a gold bond pad supported on the ferrule device side;

c) an electrically non-conductive insulator comprising an insulator outer surface extending to an insulator device side spaced from an insulator body fluid side, wherein the insulator disposed in the ferrule opening is hermetically sealed to the ferrule by a first gold braze so that when the ferrule is attached to an opening in a housing of an AMD, the ferrule and insulator body fluid sides, and the ferrule and insulator device sides reside outside and inside the AMD, respectively, and wherein at least one insulator via hole extends to the insulator device and body fluid sides;

d) an insulator internal metallization disposed in the insulator via hole;

e) a terminal pin residing in the insulator via hole where a second gold braze hermetically seals the terminal pin to the insulator internal metallization, wherein the terminal pin extends to a terminal pin first end spaced from a terminal pin second end, and wherein at least the terminal pin first end extends outwardly beyond the insulator device side;

f) a filter capacitor disposed at or adjacent to the insulator device side, the filter capacitor comprising:

i) a capacitor dielectric comprising a dielectric outer surface extending to a dielectric first major face spaced from a dielectric second major face;

ii) at least one active electrode plate and at least one ground electrode plate supported in the capacitor dielectric in an interleaved, partially overlapping capacitive relationship;

iii) a dielectric passageway extending into the capacitor dielectric from the dielectric first major face adjacent to the insulator device side;

iv) a capacitor internal metallization disposed in the iv) dielectric passageway and being conductively connected to the at least one active electrode plate, wherein the outwardly extending terminal pin first end resides in the dielectric passageway where the terminal pin is conductively connected to the capacitor internal metallization connected to the at least one active electrode plate by a first conductive material; and v) a capacitor external metallization disposed on at least a first portion and a spaced-apart second portion of the dielectric outer surface to provide terminated first and second dielectric outer surface portions that are separated from each other by intermediate and unterminated third and fourth dielectric outer surface portions, wherein the at least one ground electrode plate extends to the terminated first and second dielectric outer surface portions, and the at least one ground electrode plate either does or does not extend to the unterminated third and fourth dielectric outer surface portions; and g) a second conductive material connecting the terminated first portion of the capacitor external metallization to at least one of the first gold braze sealing the insulator to the ferrule or the gold bond pad supported on the ferrule device side; and h) a third conductive material connecting the terminated second portion of the capacitor external metallization to the exposed layer of titanium oxide on the ferrule device side, spaced outwardly beyond the first gold braze, wherein the third conductive material does not contact the first gold braze sealing the insulator to the ferrule or the gold bond pad supported on the ferrule device side.

18. The EMI filtered feedthrough of claim 17, wherein, in a plan view looking at the dielectric first major face, the capacitor dielectric has a rectangular shape comprising opposed dielectric first and second long sides extending to and meeting with opposed dielectric third and fourth short ends, and wherein the at least one ground electrode plate extends to the dielectric first and second long sides comprising the spaced-apart terminated first and second dielectric outer surface portions, but the ground electrode plate does not extend to the dielectric third and fourth short ends comprising the unterminated third and fourth dielectric outer surface portions of the capacitor dielectric.

19. The EMI filtered feedthrough of claim 17, wherein the gold bond pad is spaced outwardly from the first gold braze sealing the insulator to the ferrule.

\*    \*    \*    \*    \*